US011185530B2

(12) United States Patent
Choung et al.

(10) Patent No.: US 11,185,530 B2
(45) Date of Patent: Nov. 30, 2021

(54) COMPOSITION FOR PREVENTING OR TREATING HEARING LOSS, CONTAINING ATORVASTATIN AS ACTIVE INGREDIENT

(71) Applicant: AJOU UNIVERSITY INDUSTRY-ACADEMIC COOPERATION FOUNDATION, Gyeonggi-do (KR)

(72) Inventors: Yun-Hoon Choung, Seoul (KR); Yun Yeong Lee, Gyeonggi-do (KR); Oak-Sung Choo, Gyeonggi-do (KR)

(73) Assignee: AJOU UNIVERSITY INDUSTRY-ACADEMIC COOPERATION FOUNDATION, Gyeonggi-Do (KR)

( * ) Notice: Subject to any disclaimer, the term of this patent is extended or adjusted under 35 U.S.C. 154(b) by 59 days.

(21) Appl. No.: 16/488,881

(22) PCT Filed: Mar. 9, 2018

(86) PCT No.: PCT/KR2018/002810
§ 371 (c)(1),
(2) Date: Aug. 26, 2019

(87) PCT Pub. No.: WO2018/164526
PCT Pub. Date: Sep. 13, 2018

(65) Prior Publication Data
US 2020/0022954 A1 Jan. 23, 2020

(30) Foreign Application Priority Data

Mar. 9, 2017 (KR) .......................... 10-2017-0030075
Mar. 9, 2017 (KR) .......................... 10-2017-0121258

(51) Int. Cl.
*A61K 31/40* (2006.01)
*A61P 27/16* (2006.01)
*A61K 9/28* (2006.01)

(52) U.S. Cl.
CPC ................ *A61K 31/40* (2013.01); *A61K 9/28* (2013.01); *A61P 27/16* (2018.01)

(58) Field of Classification Search
CPC .................................. A61K 31/40; A61P 27/16
See application file for complete search history.

(56) References Cited

U.S. PATENT DOCUMENTS

| | | | |
|---|---|---|---|
| 6,235,311 B1 * | 5/2001 | Ullah .................... | A61K 9/5084 424/472 |
| 8,541,466 B2 | 9/2013 | DeLong et al. | |
| 9,150,533 B2 * | 10/2015 | Whitlon ............. | A61K 31/4418 |
| 2014/0179723 A1 | 6/2014 | Whitlon et al. | |
| 2016/0022663 A1 * | 1/2016 | Whitlon ............... | A61K 31/216 514/311 |

FOREIGN PATENT DOCUMENTS

KR 101831947 B1 2/2018

OTHER PUBLICATIONS

Rydgren et al. (Simvastatin protection against murine type 1 diabetes. The journal of pharmacology and experimental therapeutics 2007, vol. 323, No. 1) (Year: 2007).*
National Institute of Health (News releases. Hearing loss is common in people with diabetes, 2008) (Year: 2008).*
Cunningham et al The New England journal of Medicine 377;25, Dec. 21, 2017 Review Article: Hearing loss in adults. (Year: 2017).*
Arjun et al Iranian journal of otorhinolaryngology Sep. 2015; 27(82); 355-359. Sudden Sensorineural Hearing Loss; Prognostic Factors (Year: 2015).*
Park et al. Acta Oto-Laryngologica, 2009; 166-174. Simvastatin treatment induces morphology alterations and apoptosis in murine cochlear neuronal cells (Year: 2009).*
Surwit, R. S., et al. "Differential effects of fat and sucrose on the development of obesity and diabetes in C57BL/6J and AJ mice." Metabolism 44.5 (1995): 645-651.*
Surwit, Richard S., et al. "Diet-induced type II diabetes in C57BL/6J mice." Diabetes 37.9 (1988): 1163-1167.*
Dissard, Romain, et al. "Long term metabolic syndrome induced by a high fat high fructose diet leads to minimal renal injury in C57BL/6 mice." PloS one 8.10 (2013): e76703.*
Lerman-Garber, Israel, et al. "Sensorineural Hearing Loss—A Common Finding in Early-Onset Type 2 Diabetes Me Llitus." Endocrine Practice 18.4 (2012): 549-557.*
Chen, Zhi-yu, et al. "Atorvastatin helps preserve pancreatic β cell function in obese C57BL/6 J mice and the effect is related to increased pancreas proliferation and amelioration of endoplasmic-reticulum stress." Lipids in health and disease 13.1 (2014): 1-10.*
Syka, Josef, et al. "Atorvastatin slows down the deterioration of inner ear function with age in mice." Neuroscience letters 411.2 (2007): 112-116.*
Remington, Joseph Price. Remington: The science and practice of pharmacy. Eds. David B. Troy, and Paul Beringer. Lippincott Williams & Wilkins (2006) 929-932.*

(Continued)

*Primary Examiner* — Bethany P Barham
*Assistant Examiner* — Peter Anthopolos
(74) *Attorney, Agent, or Firm* — Hultquist, PLLC; Steven J. Hultquist

(57) ABSTRACT

The present invention relates to a composition for preventing or treating hearing loss, containing an HMG-CoA reductase inhibitor and, more specifically, to a composition for preventing or treating diabetes-mediated hearing loss, containing, as an active ingredient(s), one or more types selected from the group consisting of atorvastatin, fluvastatin, lovastatin, pitavastatin, pravastatin, rosuvastatin and simvastatin. A pharmaceutical composition containing an HMG-CoA reductase inhibitor, according to the present invention, inhibits auditory cell death caused by diabetes, and thus is very useful as an agent for preventing or treating diabetes-mediated sensorineural hearing loss.

8 Claims, 7 Drawing Sheets
(6 of 7 Drawing Sheet(s) Filed in Color)

(56) References Cited

OTHER PUBLICATIONS

Borghi, C., et al., "Possible Role of HMG-CoA Reductase Inhibitors for the Treatment of Sudden Sensorineural Hearing Loss (SSHL)", "Medical Hypotheses", 2002, pp. 399-402, vol. 58, No. 5.

Olzowy, B., et al., "Effect of Atorvastatin on Progression of Sensorineural Hearing Loss and Tinnitus in the Elderly Results of a Prospective, Randomized, Double-Bind Clinical Trial", "Otology and Neurology", 2007, pp. 455-458, vol. 28.

Syka, J., et al., "Atorvastatin Slows Down the Deterioration of Inner Ear Function with Age in Mice", "Neuroscience Letters", 2007, pp. 112-116, vol. 411.

Baek, M.J., "Sensorineural Hearing Loss: Causes and Hearing Rehabilitation", "Hanyang Medical Reviews", 2015, pp. 57-65, vol. 35.

Bonetti, P.O., et al., "Statin Effects Beyond Lipid Lowering—Are They Clinically Relevant?", "European Heart Journal", 2003, pp. 225-248, vol. 24.

Chen, A., et al., "Lipids in Health and Disease", 2014, pp. 1-10, vol. 13, No. 98.

Evans, M.B., et al., "Dyslipidemia and Auditory Function", "Otology and Neurotology", 2006, pp. 609-614, vol. 27.

Goldstein, M., et al., "Cholesterol, Statins, and Mortality", "Lancet", Apr. 5, 2008, p. 1161, vol. 371.

Jahani, L., et al., "The Effect of Atorvastatin on Preventing Noise-Induced Hearing Loss: An Experimental Study", "Intl J Occup Environ Med", Jan. 2016, pp. 15-21, vol. 7, No. 1.

Liu, L., et al., "Effect of Atorvastatin on Tumor Growth and Metastasis in a Breast Cancer Cell Xenograft Model and its Mechanism", "Front. Med. China", 2009, pp. 443-446, vol. 3, No. 4.

Mihaylowa. B., et al., "The Effects of Lowering LDL Cholesterol With Statin Therapy in People at Low Risk of Vascular Disease: Meta-analysis of Individual Data from 27 Randomised Trials", "Lancet", Aug. 11, 2012, pp. 581-590, vol. 380.

Rydgren, T., et al., "Simvastatin Protects Against Multiple Low Dose Streptozotocin Induced Type 1 Diabetes in CD-1 Mice and Recurrence of Disease in Non Obese Diabetic Mice", "Journal of Pharmacology and Experimental Therapeutics", Jul. 17, 2007, pp. 1-32.

Chung, S-D, et al., "A Population-Based on the Association between Statin Use and Sudden Sensorineural Hearing Loss", Otolaryngology—Head and Neck Surgery, 2015, pp. 319-325, vol. 152, No. 2, Publisher American Academy of Otolaryngology—Head and Neck Surgery.

Kim, S.Y., et al., "Association Between Sudden Sensorineural Hearing Loss and History of Statin Use: A Nested Case-Control Study", Otolaryngology—Head and Neck Surgery, 2020, pp. DOI:10. 1177/0194599820969630, Publisher: American Academy of Otolaryngology—Head and Neck Surgery.

\* cited by examiner

A

B

COMPOSITION FOR PREVENTING OR TREATING HEARING LOSS, CONTAINING ATORVASTATIN AS ACTIVE INGREDIENT

CROSS-REFERENCE TO RELATED APPLICATIONS

This application is a U.S. national phase under the provisions of 35 U.S.C. § 371 of International Patent Application No. PCT/KR18/02810 filed Mar. 9, 2018, which in turn claims priority of Korean Patent Application No. 10-2017-0030075 filed Mar. 9, 2017 and Korean Patent Application No. 10-2017-0121258 filed Mar. 9, 2017. The disclosures of International Patent Application No. PCT/KR18/02810, Korean Patent Application No. 10-2017-0030075, and Korean Patent Application No. 10-2017-0121258 are hereby incorporated herein by reference in their respective entireties, for all purposes.

TECHNICAL FIELD

The present invention relates to a composition for preventing or treating hearing loss containing an HMG-CoA reductase inhibitor, and more specifically to a composition for preventing or treating diabetes-mediated hearing loss, containing, as an active ingredient, one or more selected from the group consisting of atorvastatin, fluvastatin, lovastatin, pitavastatin, pravastatin, rosuvastatin and simvastatin.

BACKGROUND ART

Hearing loss is mainly caused by environmental factors and genetic factors such as sporadicalness, medications (such as antibiotics or anticancer drugs), noise, trauma, senility and congenital factors, and is often sensorineural hearing loss caused by damage to and death of auditory cells. For the treatment of sensorineural hearing loss, signaling pathway mechanisms involved in the regeneration of inner ear hair cells and the proliferation and differentiation of hair cells have been actively identified, and, in recent years, research on regeneration of hair cells has rapidly progressed through the development of technologies associated with gene therapy (gene editing) or cell transplantation (Hanyang Med Rev, 2015). However, the development of mechanisms or preventive or therapeutic agents associated with the inhibition and prevention of hearing loss remains unsatisfactory (Hanyang Med Rev, 2015).

According to an International Diabetes Federation (IDF) report in 2014, approximately 387 million people, corresponding to 8.3% of the world's population, are estimated to be diabetic. The association between diabetes and hearing loss has been known since the 1980s, and many reports have been published stating that diabetes may cause damage to the nerves and blood vessels of the inner ear, thus frequently resulting in hearing loss or having a significant effect on hearing. The US NIH (1995) and ADA (2014) research reported that diabetes causes microvascular and neurologic complications, which may cause damage to the vascular and nervous systems of the inner ear and may affect sensorineural hearing loss. In addition, the results of research on the relationship between diabetes and hearing loss through diabetes-induced animals have shown that persistent hyperglycemia for about 2 months causes hearing loss due to damage to auditory nerves, such as peripheral neuropathy, which is one diabetic complication (Neurosci. Lett., 2008). Hyperlipemia commonly occurs in diabetes patients and affects the onset of diabetic complications. It has been suggested that dyslipidemia may have sensitive effects on the functions of outer ear hair cells and the progression of age-related hearing loss (presbycusis) such as hyperlipidemia, lipidosis and hypertension is associated with high-frequency threshold loss. In addition, the increase in triglyceride is meaningful as a predictor of the decline in auditory sensation (Otol Neurotol, 2006), and a South Korea National Health and Nutrition Examination Survey and a Korea National Health and Nutrition Examination Survey (2010-2012) reported that chronic diseases such as diabetes, hypertension, and hyperlipidemia are factors causing hearing loss, and suggested that chronic diseases are closely related to hearing loss. However, a clear pathogenesis of hearing loss due to chronic diseases has not yet been found.

It is known that statins are one of the most commonly prescribed drugs in the world and have the effect of inhibiting atherosclerosis in the coronary arteries by relieving inflammation of the coronary arteries (Hs-CRP) and stabilizing the thrombus (plaque stability). In addition, they have been shown to have an effect of treating cardiovascular diseases including hypertension by inhibiting the contraction of blood vessels (Lancet, 2008, 2012; Eur Heart J, 2003). Among statins, atorvastatin is known to inhibit the inflammatory response of vascular endothelial cells, thereby maintaining the functions of the inner ear of the auditory organ in the mouse model of age-related hearing loss and delaying or inhibiting hearing loss (Neuroscience Letters, 2007). It has been reported that a low dose of atorvastatin (5 mg/kg) has a statistically significant effect of inhibiting hearing loss in the noise-induced hearing loss rat model (The International Journal of Occupational and Environmental Medicine, 2016). In the breast cancer cell xenograft model, atorvastatin has been reported to inhibit tumor growth and metastasis by increasing the activity of JNK, which is a tumor stress protein marker, and decreasing activity of ERK and AKT protein (Front. Med. China, 2009). In addition, it has been reported that atorvastatin inhibits obesity-induced type 2 diabetes by alleviating endoplasmic reticulum (ER) stress in pancreatic beta-cells and promoting cell growth in obese C57 mice (Lipids in Health and Disease, 2014). In addition, atorvastatin has been reported to inhibit obesity-induced type 2 diabetes by alleviating the stress of endoplasmic reticulum (ER) in pancreatic β cells and promoting cell growth in obese C57 mice (Lipids in Health and Disease, 2014). In addition, simvastatin has been reported to inhibit or delay diabetes by inhibiting the inflammatory response of pancreatic beta cells and thus maintaining functions in a molecular biological mouse model with type 1 diabetes induced by streptozotocin (Journal of Pharmacology and Experimental Therapeutics, 2007).

Recent research results have shown that hearing loss is closely related to various chronic diseases such as diabetes and hyperlipidemia. However, they failed to suggest clear molecular mechanism research for the prevention and treatment of hearing loss, and treatment methods thereof.

Therefore, as a result of extensive efforts to prevent and treat diabetes-mediated hearing loss (deafness) through identification of the pathogenesis of hearing loss (deafness) caused by chronic diseases such as diabetes, the present inventors have found that HMG-CoA reductase inhibitors are capable of alleviating hearing loss (deafness) as well as diabetes, and inhibiting deterioration in hearing in the diabetic mouse model and cell line model. Based on this finding, the present invention has been completed.

DISCLOSURE

Technical Problem

Therefore, the present invention has been made in view of the above problems, and it is one object of the present invention to provide a pharmaceutical composition for preventing or treating hearing loss containing an HMG-CoA reductase inhibitor as an active ingredient and a tablet containing the composition.

It is another object of the present invention to provide a method of treating hearing loss including administering a pharmaceutical composition for preventing or treating hearing loss containing an HMG-CoA reductase inhibitor as an active ingredient and a tablet containing the composition.

It is another object of the present invention to provide the use of a pharmaceutical composition containing an HMG-CoA reductase inhibitor as an active ingredient and a tablet containing the composition for the treatment of hearing loss.

Technical Solution

In accordance with one aspect of the present invention, the above and other objects can be accomplished by the provision of a pharmaceutical composition for preventing or treating hearing loss containing an HMG-CoA reductase inhibitor as an active ingredient.

In accordance with another aspect of the present invention, there is provided a method of treating hearing loss including administering a composition containing an HMG-CoA reductase inhibitor as an active ingredient.

In accordance with another aspect of the present invention, there is provided the use of a composition containing an HMG-CoA reductase inhibitor as an active ingredient for the treatment of hearing loss.

In accordance with another aspect of the present invention, there is provided a tablet including a pharmaceutical composition for preventing or treating hearing loss containing an HMG-CoA reductase inhibitor as an active ingredient.

In accordance with another aspect of the present invention, there is provided a method of treating hearing loss including administering a tablet including a pharmaceutical composition for preventing or treating hearing loss containing an HMG-CoA reductase inhibitor as an active ingredient.

In accordance with another aspect of the present invention, there is provided the use of a tablet including a pharmaceutical composition for preventing or treating hearing loss containing an HMG-CoA reductase inhibitor as an active ingredient for the treatment of hearing loss.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Figure 1:
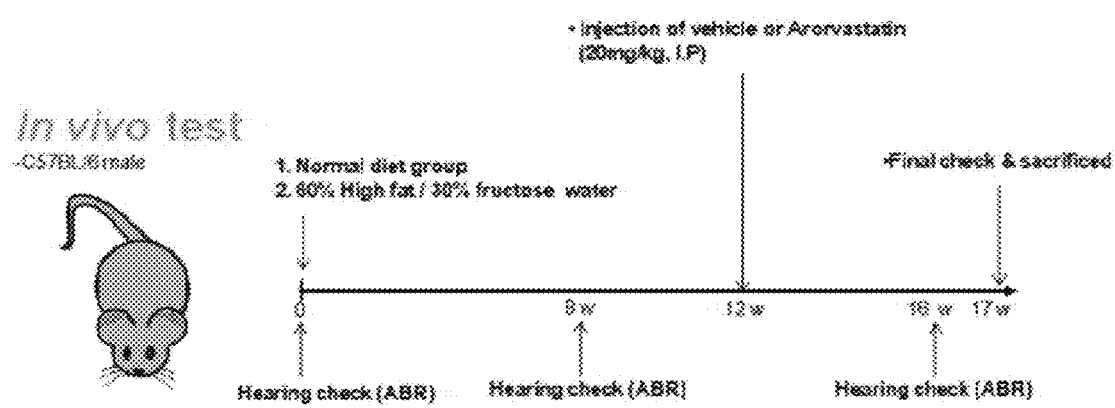
FIG. 1 is a schematic diagram of an in-vivo test.

Unless defined otherwise, all technical and scientific terms used herein have the same meanings as appreciated by those skilled in the field to which the present invention pertains. In general, the nomenclature used herein is well-known in the art and is ordinarily used.

In the present invention, hearing and diabetes are found to be alleviated through inhibition of apoptosis and maintenance of mitochondrial energy (ATP) by establishing diabetic mouse models and diabetes-mediated hearing loss cell lines and then treating the same with atorvastatin, which is an HMG-CoA reductase inhibitor. That is, the effects of the HMG-CoA reductase inhibitor on alleviation or treatment of diabetes-mediated hearing loss were identified.

Thus, in one aspect, the present invention is directed to a pharmaceutical composition for preventing or treating hearing loss containing an HMG-CoA reductase inhibitor as an active ingredient.

"HMG-CoA reductase inhibitor" or "statin" according to the present invention is known as a lipid-suppressor inhibiting cardiovascular disease (CVD), which inhibits HMG-CoA reductases, which play an important role in cholesterol production.

In the present invention, the HMG-CoA reductase inhibitor preferably includes one or more selected from the group consisting of atorvastatin, fluvastatin, lovastatin, pitavastatin, pravastatin, rosuvastatin and simvastatin, more preferably atorvastatin, but the present invention is not limited thereto.

As herein used, the term "hearing loss" includes conductive hearing loss and sensorineural hearing loss. Conductive hearing loss is hearing loss that occurs when the transmission of sound waves is not normally performed due to an obstacle to the organ that delivers sounds such as the outer ear, eardrum, middle ear, and the like, and sensorineural hearing loss is hearing loss caused by abnormalities in the function of detecting the sound in the cochlea or abnormalities in the auditory nerve or the central nervous system that delivers auditory stimuli to the brain. Sensorineural hearing loss is due to a wide variety of causes, including inflammatory diseases such as labyrinthitis or myocarditis, noise-induced hearing loss, toxic drugs, trauma such as temporal bone fractures, senile hearing loss, Meniere's disease, sudden sensorineural hearing loss, metabolic disorders such as decreased thyroid function, ischemic diseases of the brain, blood diseases such as leukemia, neurological disorders such as multiple sclerosis, immunologic disorders, neoplastic diseases such as auditory neuropathy, and bone diseases.

Sensorineural hearing loss as referred to in the present invention may be caused by damage to inner ear hair cells and surrounding tissues.

In the present invention, the hearing loss is preferably sensorineural hearing loss, more preferably diabetes-mediated hearing loss caused by diabetes, but the present invention is not limited thereto.

In the present invention, the composition containing an HMG-CoA reductase inhibitor may be characterized by inhibiting apoptosis of auditory cells, promoting AKT phosphorylation, or maintaining ATP production, and may be further characterized by reducing insulin tolerance or glucose tolerance.

In a specific embodiment of the present invention, the composition containing an HMG-CoA reductase inhibitor may be formulated into any one selected from the group consisting of an injection, a granule, a powder, a tablet, a pill, a capsule, a suppository, a gel, a suspension, an emulsion, a dropping agent and a liquid.

In another embodiment of the present invention, the composition containing an HMG-CoA reductase inhibitor may further contain at least one additive selected from the group consisting of additives commonly used for the preparation of compositions including suitable carriers, excipients, disintegrants, sweeteners, coatings, swelling agents, lubricants, slip modifiers, flavors, antioxidants, buffers, bacteriostats, diluents, dispersants, surfactants, binders and lubricants.

Specifically, the carrier, excipient or diluent may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration may be tablets, pills, powders, granules, capsules and the like, and may be prepared by mixing at least one excipient, for example, starch, calcium carbonate, sucrose, lactose, gelatin or the like. In addition to simple excipients, lubricants such as magnesium stearate and talc are also used. Liquid formulations for oral administration may be suspensions, oral liquids and solutions, emulsions, syrups and the like, and may include various excipients such as wetting agents, sweeteners, fragrances, preservatives and the like, in addition to water and liquid paraffin, which are simple diluents that are commonly used. Formulations for parenteral administration may be sterilized aqueous solutions, non-aqueous solutions, suspensions, emulsions, freeze-dried preparations and suppositories. Examples of non-aqueous solutions and suspensions include propylene glycol, polyethylene glycol, vegetable oil such as olive oil, injectable ester such as ethyl oleate, and the like. Examples of the suppository base include Witepsol, macrogol, Tween 61, cacao butter, laurin butter, glycerogelatin and the like.

The pharmaceutical composition according to the invention may be administered orally (e.g., by ingestion or inhalation) or parenterally (e.g., by injection, deposition, implantation, suppository), and the injection may be intravenous, subcutaneous, intramuscular or intraperitoneal injection. The pharmaceutical composition according to the present invention may be formulated into tablets, capsules, granules, fine subtilaes, powders, sublingual tablets, suppositories, ointments, injections, emulsions, suspensions, syrups, sprays or the like. The various forms of the pharmaceutical composition according to the present invention can be prepared through a known technique using a pharmaceutically acceptable carrier commonly used in each formulation. Examples of the pharmaceutically acceptable carrier include excipients, binders, disintegrating agents, lubricants, preservatives, antioxidants, isotonic agents, buffers, coating agents, sweeteners, solubilizers, bases, dispersants, wetting agents, suspending agents, stabilizers, coloring agents and the like.

The pharmaceutical composition according to the present invention contains about 0.01 to 95% by weight of the compound of the present invention (HMG-CoA reductase inhibitor), which depends on the form of the drug.

The dose (used amount) of the HMG-CoA reductase inhibitor, which is an active ingredient of the pharmaceutical composition according to the present invention, may vary depending on the age, gender, body weight and disease of the patient, but is preferably 0.001 to 100 mg/kg, more preferably 0.01 to 10 mg/kg, which may be administered once to several times a day.

In addition, the dosage (administered amount) of the HMG-CoA reductase inhibitor according to the present invention may be increased or decreased depending on the route of administration, disease severity, gender, body weight, age, and the like. Thus, the dosage is not intended to limit the scope of the invention in any aspect.

The pharmaceutical composition may be administered to mammals such as rats, mice, livestock and humans via a variety of routes. All modes of administration may be considered, for example, by oral, rectal, intravenous, intramuscular or subcutaneous administration, endotracheal inhalation, or intrauterine cervical or intracerebroventricular injection.

The composition of the present invention can be used alone or in combination with methods using surgery, hormone therapy, medication therapy and biological response modifiers for the prevention or treatment of hearing loss.

In another aspect, the present invention is directed to a method of treating hearing loss including administering a composition containing an HMG-CoA reductase inhibitor as an active ingredient.

In another aspect, the present invention is directed to the use of a composition containing an HMG-CoA reductase inhibitor as an active ingredient for the treatment of hearing loss.

In another aspect, the present invention is directed to a tablet including a composition containing the HMG-CoA reductase inhibitor.

In the present invention, the tablet is preferably a coated form, but the present invention is not limited thereto.

In another aspect, the present invention is directed to a method for treating hearing loss including administering a tablet containing the composition containing the HMG-CoA reductase inhibitor.

In another aspect, the present invention is directed to the use of a tablet containing a composition containing the HMG-CoA reductase inhibitor for the treatment of hearing loss.

In another aspect, the present invention is directed to a food composition for preventing or alleviating hearing loss containing an HMG-CoA reductase inhibitor as an active ingredient.

The food composition may be provided in the form of a powder, granule, tablet, capsule, syrup or beverage. The health food may be used in combination with other food or food additives other than the HMG-CoA reductase inhibitor, which is an active ingredient, and can be suitably used in accordance with a conventional method. The amount of the active ingredient to be mixed therewith can be suitably determined according to the use purpose thereof, for example, prevention, health or therapeutic treatment.

The effective dose of the HMG-CoA reductase inhibitor contained in the food composition may be used in accordance with the effective dose of the pharmaceutical composition. However, in the case of long-term intake for the purpose of health and hygiene or for the purpose of health management, the effective dose may be within the range defined above, and it will be obvious that the active ingredient can be used in an amount exceeding the above range because there is no problem in terms of safety.

There is no particular limitation as to the kind of the food composition. Examples of the food composition include meat, sausage, bread, chocolate, candy, snacks, confectionery, pizza, ramen, other noodles, gum, dairy products including ice cream, various soups, beverages, tea, drinks, alcoholic beverages, vitamin complexes and the like.

EXAMPLE

Hereinafter, the present invention will be described in more detail with reference to examples. However, it will be obvious to those skilled in the art that these examples are provided only for illustration of the present invention and should not be construed as limiting the scope of the present invention based on the subject matter of the present invention.

Example 1: Establishing Diabetic Mouse Model for In-Vivo Test

A total of 68 C57/BL6J male mice were divided into a normal group (n=15) and a diabetes-induced group (n=53). Auditory brainstem response (ABR) pre-hearing tests were performed on all mice to exclude mice exhibiting abnormal hearing for congenital reasons. Bursts of tones with frequencies of 16 kHz and 32 kHz were applied using a TDT ABR device, and the minimum stimulation tone (sound) level (dB) at which the waveform of the wave V appeared was determined as to be the hearing threshold. The diabetes induction process before drug administration and the hearing ability of the experimental group and the control group after drug administration were measured for 0, 8, and 16 weeks, and the effects of inducing or preventing hearing loss were comparatively analyzed, and statistical significance was identified.

The diabetes-mediated hearing loss model was fed with 60% high fat/30% fructose water for 12 weeks and bred to induce diabetes. The diabetes model was established by measuring blood glucose levels, and testing glucose tolerance and insulin tolerance once every two weeks for 12 weeks, weighing weekly and conducting food/water intake efficiency tests twice weekly. Upon induction of diabetes, over 220 mg/dl of blood glucose level, the statistical significance of insulin/glucose tolerance, and diabetes and diabetes-mediated hearing loss depending on the presence or absence of hearing abnormalities were determined, subjects not meeting selection requirements were excluded, and ultimately, 30 animals were reclassified into the experimental group and the control group.

The experimental group was divided into an atorvastatin group (n=15, 20 mg/kg) and a control (vehicle) group (n=15, DMSO+normal saline) and intraperitoneal administration was conducted once every 2 days for 5 weeks. During the drug administration period, body weight and food intake efficiency tests were performed. Hearing tests, blood glucose measurement, and glucose and insulin tolerance tests were performed immediately before the end of the administration period.

Figure 2:
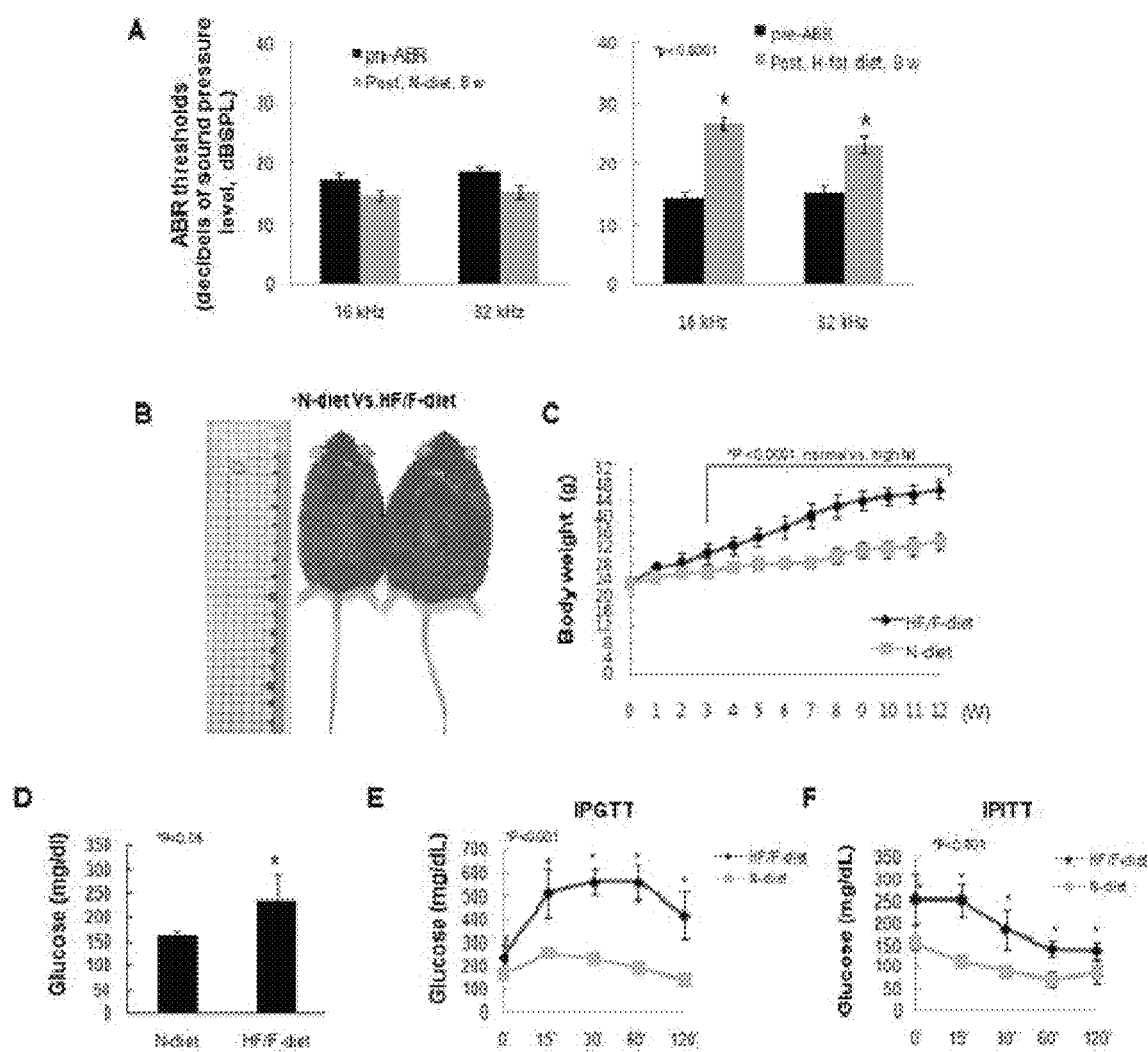
FIG. 2 in the graphs shown in part A shows the result of measurement of the left and right auditory brainstem responses (ABR) in a mouse fed with a normal diet (left graph) and a mouse fed with a high fat/fructose diet (right graph), FIG. 2 in part B shows a comparison of the body size between the mouse fed with the normal diet (left) and the mouse fed with the high fat/fructose diet (right) for 12 weeks, FIG. 2 in part C shows the analysis result of body weight changes, FIG. 2 in part D shows the analysis result of the blood glucose level, FIG. 2 in part E shows the analysis result of glucose tolerance (GTT), and FIG. 2 in part F shows the analysis result of insulin tolerance (ITT)

Example 2: Identification of Hearing Change and Diabetes Induction in Diabetic Mouse Model The auditory brainstem response (ABR) test was performed in the $8^{th}$ week of the process of inducing diabetes by breeding mice while feeding with 60% high fat/30% fructose water for 12 weeks. As a result, hearing thresholds of both ears of the mice at 16 kHz and 32 kHz were statistically significantly increased and hearing loss was clearly observed (FIG. 2 in part A).

Then, body size, body weight, blood glucose, glucose tolerance and insulin tolerance of the diabetes-induced mouse model were measured 12 weeks after diabetes induction. As a result, the body size and body weight increased statistically with a statistically significant difference (FIG. 2 in parts B and C) after 3 weeks, and blood glucose level (FIG. 2 in part D), glucose tolerance (FIG. 2 in part E) and insulin tolerance (FIG. 2 in part F) of the diabetes-induced mouse model differed significantly from those of the normal group.

These results indicate that the mice can be determined to be finally diabetic, and as a result, it is found that the diabetes is accompanied by hearing loss in the high-fat/fructose diet diabetic mouse model.

Example 3: Identification of Changes in Hearing Ability and Alleviation of Diabetes Before and After Administration of Atorvastatin to Diabetic Mouse Model The auditory brainstem response (ABR) of the experimental group, that is, the $12^{th}$-week diabetes-induced mouse model fed with a high-fat/fructose diet and administered with atorvastatin (20 mg/kg) once every two days for 5 weeks, and of the control group administered with normal saline was tested.

Figure 3:
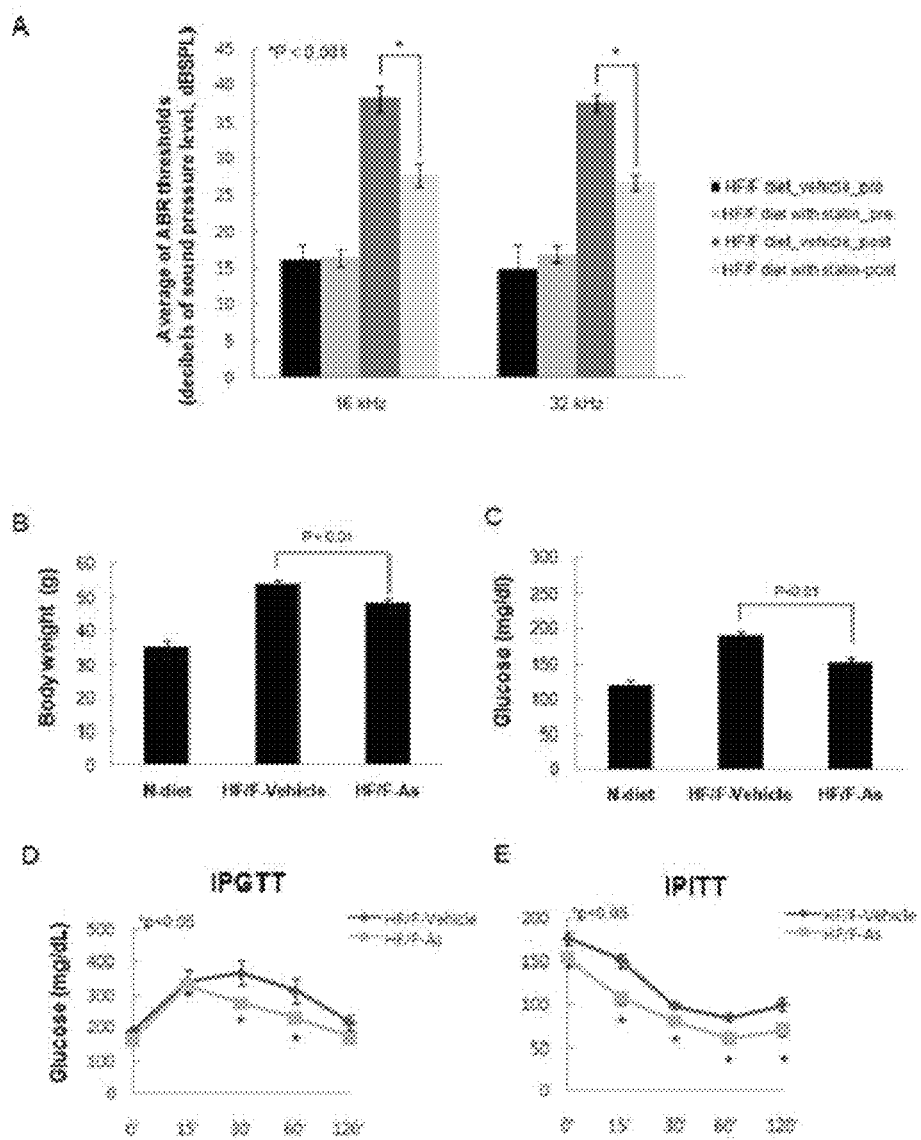
FIG. 3 shows the effects of hearing and diabetes before/after administration of atorvastatin to diabetic mice (high fat/fructose diet, at 12 weeks), more specifically, FIG. 3 in part A shows the result of measurement of the left and right auditory brainstem responses (ABR) in the mouse fed with the normal diet (left) and the mouse fed with the high fat/fructose diet (right), FIG. 3 in part B showing changes in body weight after 12 weeks, FIG. 3 in part C shows the result of analysis of blood glucose level, FIG. 3 in part D shows the result of analysis of glucose tolerance (GTT), and FIG. 3 in part E shows the result of analysis of insulin tolerance (ITT)

As a result, the hearing thresholds of both ears of the control group at 16 kHz and 32 kHz increased by about 10 kHz on average compared to that of the $8^{th}$-week group, whereas the experimental group administered with atorvastatin showed a similar hearing threshold to the $8^{th}$-week group (FIG. 3 in part A). That is, it can be seen that hearing loss induced by diabetes was inhibited in the experimental group administered with atorvastatin compared to the control group.

In addition, body weight, blood glucose level, glucose tolerance and insulin tolerance were measured in the experimental group, obtained by administering atorvastatin to the 12-week diabetic mice, and in the control group. The results showed that body weight was reduced and blood glucose level, glucose tolerance and insulin tolerance were significantly improved (FIG. 3 in parts B, C, D, and E). All statistical significance was analyzed using one-way ANOVA of SPSS program and student's T-tests.

These results indicate that the group administered with atorvastatin simultaneously inhibits both diabetes and diabetes-induced hearing loss compared to the group not administered with atorvastatin.

Example 4: Cell Death (Apoptosis) of Auditory Cells by Saturated Fatty Acid Palmitate As a cell experiment model that replaces the diabetic mouse model through a high fat/fructose diet, that is, obesity, a cytotoxicity experiment model based on saturated fatty acid palmitate, which is an intermediate product of lipid synthesis that is excessively abundant during obesity, has been devised. HEI-OC1 (house-ear institute-organ of Corti 1), the auditory cell line conducting the major auditory function, was used, and the diabetes-mediated hearing loss cell line model was treated with palmitate.

Figure 4:
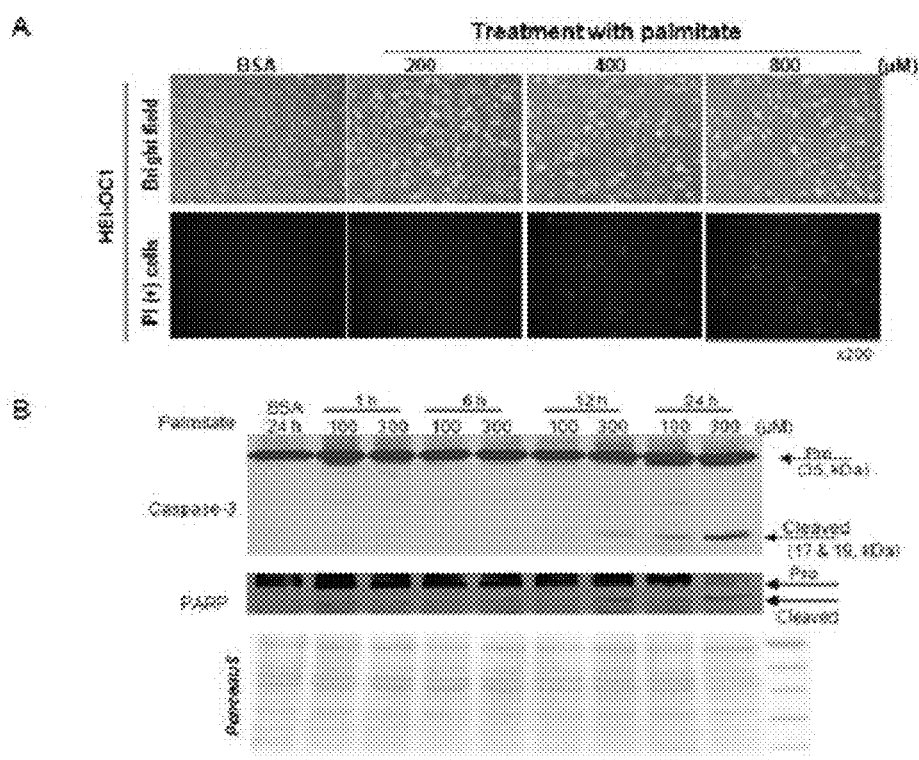
FIG. 4 in part A shows the result of apoptosis (cell death) observed after treating HEI-OC1 cells with palmitate for 24 hours, FIG. 4 in part B shows the protein levels of active caspase-3 and PARP identified through Western blotting, and FIG. 4 in part C shows the result of measurement of phosphorylation of AKT protein.
Figure 4:
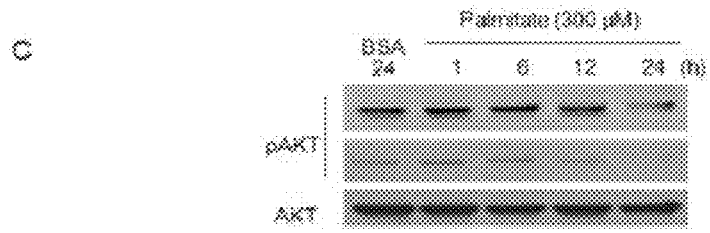

In order to evaluate apoptosis, 24 hours after HEI-OC1 cells, the auditory cell line, were treated with 200 to 800 μM of palmitate, PI (propidium iodide) staining and the cell morphology thereof were analyzed. As a result, cell apoptosis was induced with a change in cell morphology from the palmitate concentration of 200 μM, and this phenomenon became more apparent as the concentration increased (FIG. 4 in part A). In addition, analysis of cytotoxicity-induced apoptosis through apoptosis mechanism analysis revealed that the cleaved caspase-3 and PARP proteins were increased (FIG. 4 in part B), while phosphorylation of AKT protein, known as an essential protein for cell survival, was decreased (FIG. 4 in part C).

In conclusion, palmitate reduces phosphorylation of cell survival-associated AKT proteins and activates an apoptosis mechanism to induce apoptosis. Thus, the reduction of hearing in the diabetic model fed with the high-fat/fructose diet suggests that saturated fatty acid palmitate, which is an intermediate product that accumulates due to the synthesis of excessive fatty acids, causes toxicity to the auditory organs, resulting in decreased auditory function.

Example 5: Effect of Atorvastatin on Palmitate-Induced Apoptosis

The effect of palmitate on cytotoxicity and cell viability of the auditory cell line (HEI-OC1) was quantitatively analyzed through a WST-1 assay. As a result, 24 hours after the cells were treated with palmitate at different concentrations of 100, 200 and 400 μM, apoptosis was observed in about 20 to 40% of cases. In addition, cytotoxicity was not observed in the case of treatment only with atorvastatin at 250, 500 or 1,000 nM (FIG. 5 in part A).

In order to evaluate the function of atorvastatin against the cytotoxicity of palmitate, atorvastatin was pre-treated at each concentration and palmitate was post-treated at each concentration.

Figure 5:
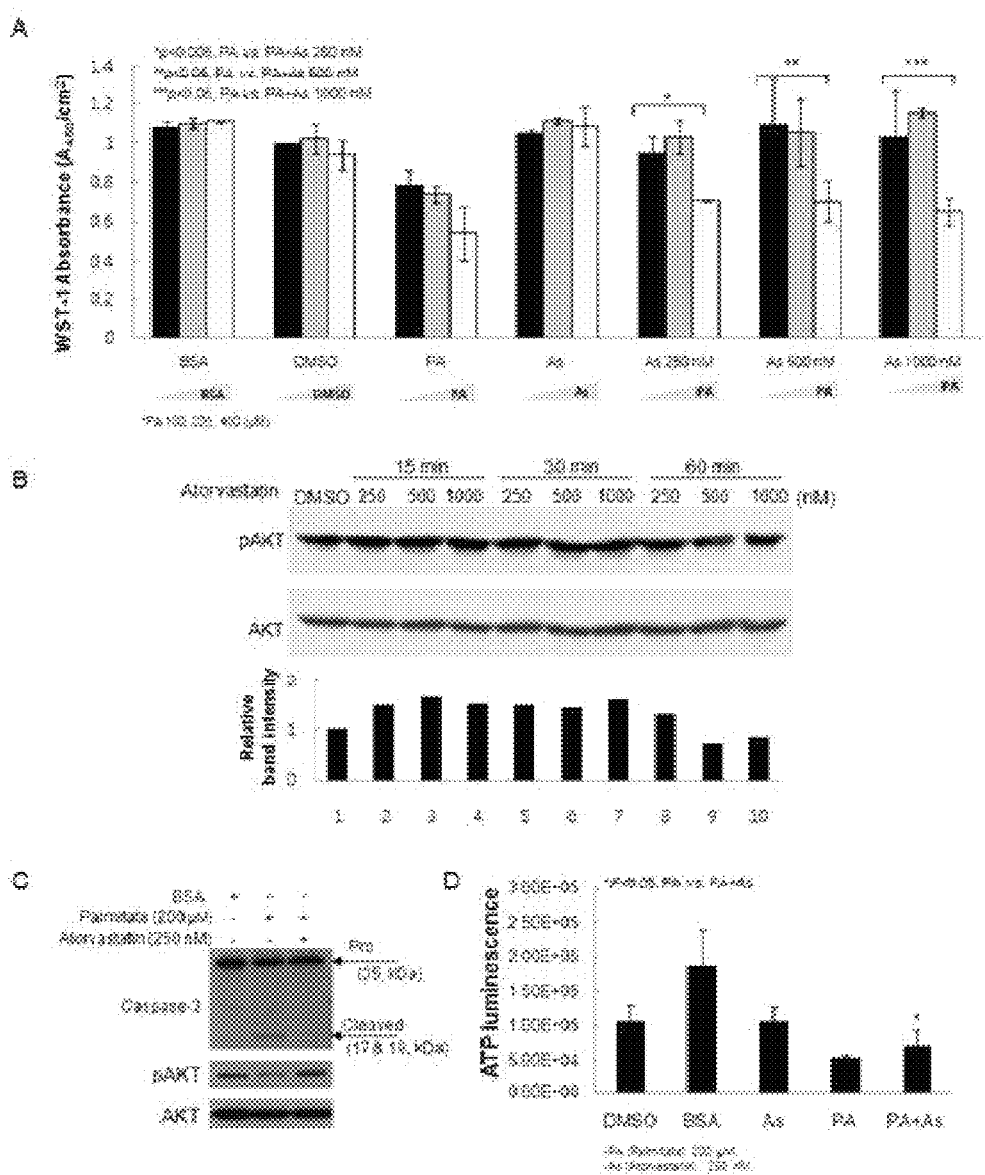
FIG. 5 shows the effect of atorvastatin on palmitate-induced apoptosis, more particularly, FIG. 5 in part A shows cell viability measured by WST-1 assay after treating a combination of palmitate and atorvastatin for 24 hours, FIG. 5 in part B shows the result of AKT phosphorylation measured on a basis of concentration and time after treatment with atorvastatin, FIG. 5 in part C shows the protein levels of active caspase-3, phosphorylated AKT and total AKT (control) identified through Western blotting, and FIG. 5 in part D shows the result of measurement of ATP content in the total extract of cells.

As a result, it was observed that apoptosis observed upon treatment only with palmitate was significantly inhibited (FIG. 5 in part A). In addition, it was found that atorvastatin increased the phosphorylation of AKT, the protein for cell survival (FIG. 5 in part B) and inhibited the reduction of AKT protein phosphorylation by treatment with palmitate (FIG. 5 in part C). In addition, the effects of atorvastatin on the protection of cells and on energy metabolisms were evaluated using ATP detection luminescence. The results showed that atorvastatin not only inhibited apoptosis due to palmitate but also maintained the production of mitochondrial energy (ATP), thereby maintaining the metabolic process of energy production, which is essential for cell survival (FIG. 5 in part D).

The cytotoxic and apoptotic effects of palmitate and the cytoprotective effect of atorvastatin were analyzed using a student's T-test for statistical significance through quantification.

These results indicate that the effect of atorvastatin on hearing protection found in diabetic model animal experiments is due to inhibition of hearing (ABR) reduction through the suppression of apoptosis of constituent cells of auditory organs, the activation of proteins essential for cell survival and the maintenance of energy production metabolic processes.

Example 6: Morphological Analysis of Cochlea of Atorvastatin-Administered and Atorvastatin-Non-Administered Diabetic Mouse Model Damage to cochlear hair cells around the base and middle turn (16 kHz) region, fibrocytes of the lateral wall and spiral ganglion cells of the cochlea of the diabetic mouse model established in Example 1 was evaluated through H & E (hematoxylin and eosin) staining and immunohistochemistry.

6-1: Analysis of Auditory Cell (Cochlear Hair Cell)

Figure 6:
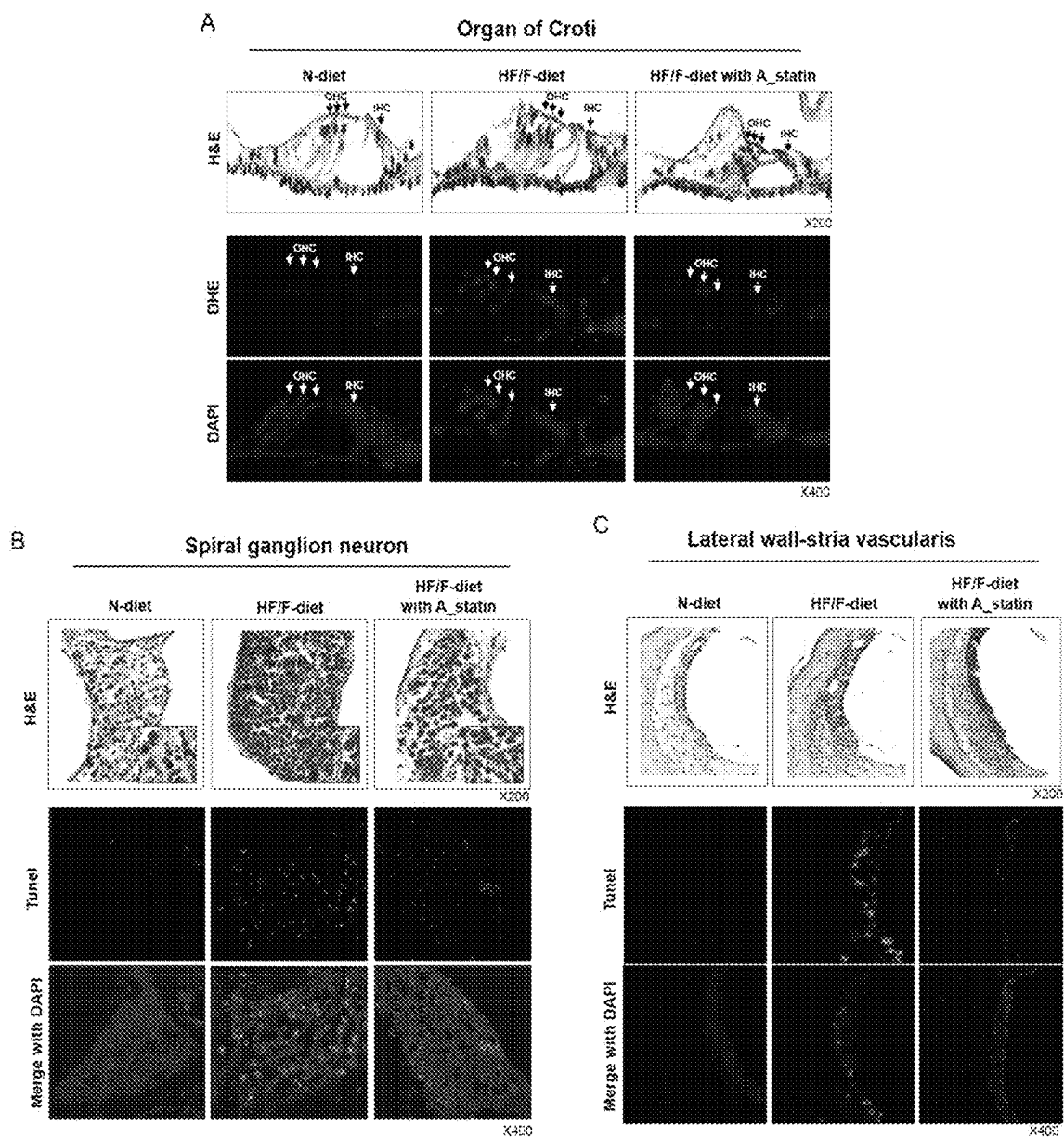
FIG. 6 shows the cochlea (inner ear, organ of corn) of diabetic mouse models administered and not administered with atorvastatin, identified by H&E staining and immunohistochemistry, more particularly, FIG. 6 in part A shows damage and functional degradation of cochlear hair cells due to reactive oxygen species, FIG. 6 in part B shows apoptosis (cell death) of spinal ganglion cells, and FIG. 6 in part C shows apoptosis (cell death) of lateral wall-stria vascularis cells.

The observation results of the morphology of the cochlear hair cells of the inner ear of diabetic mice administered with atorvastatin and diabetic mice not administered with atorvastatin showed that there were no morphological changes, like normal mice (top of FIG. 6 in part A).

Then, the auditory cells (cochlear hair cells) were observed through immunohistochemistry. As a result, dihydroethidium (DHE), which is a marker of superoxide anions, a kind of reactive oxygen species, was expressed more strongly in diabetic mice than in normal mice, which means that auditory outer and inner hair cells, supporting cells and auditory nerve fibers were continuously damaged by reactive oxygen species (middle of FIG. 6 in part A).

However, it was found that atorvastatin-administered mice exhibited decreased reactive oxygen species, like normal mice. That is, it was found that atorvastatin protected outer hair cells, inner hair cells, supporting cells and auditory nerve fibers from damage by reactive oxygen species (middle of FIG. 6 in part A).

6-2: Analysis of Spiral Ganglion Cells

The spiral ganglion cells were analyzed by H & E staining.

Diabetic mice showed a change in nucleus morphology and increased in cell size compared to normal mice, and the atorvastatin-administered mice had a larger cell size than that of the normal group, but had no change in nucleus morphology. That is, in diabetic mice, the functional degradation of spinal ganglion cells and apoptosis occurred (Top of FIG. 6 in part B).

In order to demonstrate this, immunostaining was conducted using terminal deoxynucleotidyl transferase dUTP nick-end labeling (TUNEL), which is a representative marker of apoptosis. The result showed that TUNEL was intensively expressed in the cellular nucleus of the spinal ganglion cells of diabetic mice, and this phenomenon was suppressed upon administration with atorvastatin. That is, it was found that atorvastatin inhibited the apoptosis of spinal ganglion cells due to diabetes (middle of FIG. 6 in part B).

6-3: Lateral Wall in Cochlea (Inner Ear)

Stria vascularis cells in the lateral wall in the cochlea (inner ear) were analyzed by H & E staining.

Diabetic mice have enlarged stria vascularis tissue since the size of the cells constituting the stria vascularis of the lateral wall in the cochlea became larger, and this phenomenon was not observed in the atorvastatin-administered mice (top of FIG. 6 in part C).

Similarly, immunostaining with TUNEL, a representative marker of apoptosis, showed that TUNEL expression was elevated in enlarged stria vascularis cells, which means the occurrence of apoptosis. In the mouse administered with atorvastatin, apoptosis was markedly suppressed (middle of FIG. 6 in part C).

In conclusion, the hearing (ABR) reduction of diabetic mice is caused by damage and functional degradation of cochlear hair cells by reactive oxygen species, apoptosis of spiral ganglion cells and apoptosis of lateral wall-stria vascularis cells. That is, this results in auditory brainstem response (ABR) deterioration and induces hearing loss.

However, it was found that atorvastatin-administered mice effectively blocked the above-mentioned damage. Therefore, the administration of atorvastatin prevents damage and functional degradation of cochlear hair cells due to reactive oxygen species, apoptosis of spiral ganglion cells and apoptosis of lateral wall-stria vascularis cells and the like, thereby preserving hearing and preventing hearing loss.

Example 7: Effects of Atorvastatin on Damage and Functional Degradation of Cochlear Hair Cells Due to Reactive Oxygen Species It was observed through staining of 2',7'-dichlorofluorescin diacetate (DCFDA), which is a marker of reactive oxygen species, that the level of reactive oxygen species in the cell was higher in the experimental group obtained by treating the auditory cell line (HEI-OC1) with palmitate, than in the control group. Treatment with palmitate and atorvastatin was found to statistically significantly inhibit the generation of reactive oxygen species (FIG. 7 in part A).

In order to investigate the effect of atorvastatin on apoptosis induced by palmitate, the palmitate-treated auditory cell line was immunostained with TUNEL, which is an apoptosis marker previously observed in spiral ganglion cells and stria vascularis cells of the lateral wall and then quantified by fluorescence microscopy.

Figure 7:
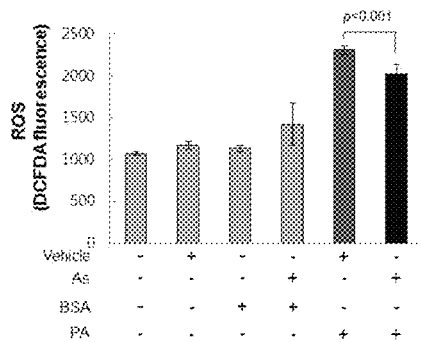
FIG. 7 in part A shows that atorvastatin inhibits generation of reactive oxygen species induced by treatment of HEI-OC1 cells with palmitate, and FIG. 7 in part B shows the effect of atorvastatin on palmitate-induced apoptosis identified by TUNEL staining.
Figure 7:
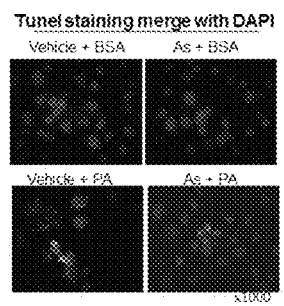
Figure 7:
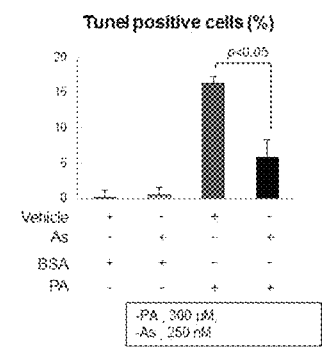

The result showed that treatment with palmitate caused cell death and increased the number of TUNEL-stained cells compared to the control group, and that the number of TUNEL-stained cells was statistically decreased in the experimental group treated with a combination of palmitate and atorvastatin (FIG. 7 in part B).

INDUSTRIAL APPLICABILITY

The pharmaceutical composition containing the HMG-CoA reductase inhibitor according to the present invention inhibits the death of auditory cells (cochlear hair cells) induced by diabetes, and thus is very useful as a preventive or therapeutic agent for diabetes-mediated sensory nerve system hearing loss.

Although specific configurations of the present invention have been described in detail, those skilled in the art will appreciate that this description is provided as preferred embodiments for illustrative purposes and should not be construed as limiting the scope of the present invention. Therefore, the substantial scope of the present invention is defined by the accompanying claims and equivalents thereto.

The invention claimed is:

1. A method for preventing or treating sensorineural hearing loss in a diabetic human in need thereof, the method comprising administering a therapeutically effective amount of atorvastatin to the diabetic human, wherein the sensorineural hearing loss is diabetes-mediated hearing loss.

2. The method according to claim 1, wherein the atorvastatin inhibits apoptosis of auditory cells, promotes AKT phosphorylation, or maintains ATP production.

3. The method according to claim 1, wherein the atorvastatin inhibits insulin tolerance or glucose tolerance.

4. The method according to claim 1, wherein the method comprises administering to the diabetic human a pharmaceutical composition containing the atorvastatin.

5. The method according to claim 4, wherein the pharmaceutical composition further comprises a pharmaceutically acceptable additive.

6. The method according to claim 5, wherein the pharmaceutically acceptable additive comprises at least one selected from the group consisting of an excipient, a binder, a slip modifier, a lubricant, a disintegrating agent, a sweetener, a flavor, and a mixture thereof.

7. The method according to claim 1, wherein the method comprises administering to the diabetic human a tablet containing the atorvastatin.

8. The method according to claim 7, wherein the tablet is coated.

* * * * *

UNITED STATES PATENT AND TRADEMARK OFFICE
CERTIFICATE OF CORRECTION

PATENT NO. : 11,185,530 B2  
APPLICATION NO. : 16/488881  
DATED : November 30, 2021  
INVENTOR(S) : Yun-Hoon Choung et al.

Page 1 of 1

It is certified that error appears in the above-identified patent and that said Letters Patent is hereby corrected as shown below:

In the Specification

Column 4, Line 34, "corn" should be -- corti --.

Signed and Sealed this  
Twenty-second Day of February, 2022

Drew Hirshfeld  
*Performing the Functions and Duties of the*  
*Under Secretary of Commerce for Intellectual Property and*  
*Director of the United States Patent and Trademark Office*